(12) United States Patent
Li et al.

(10) Patent No.: US 12,690,800 B2
(45) Date of Patent: Jul. 28, 2026

(54) MEASUREMENT METHOD AND SYSTEM BASED ON IMAGE ELECTROENCEPHALOGRAM SENSITIVITY DATA FOR BUILT ENVIRONMENT DOMINANT COLOR

(71) Applicant: SOUTHEAST UNIVERSITY, Jiangsu (CN)

(72) Inventors: Zhe Li, Jiangsu (CN); Liya Wang, Jiangsu (CN); Xiao Han, Jiangsu (CN); Futian Yuan, Jiangsu (CN); Tongyi Zhu, Jiangsu (CN); Ruoxuan Huang, Jiangsu (CN); Ying Gao, Jiangsu (CN); Yinyin Cao, Suzhou (CN); Zheng Zhou, Jiangsu (CN); Hengyi Zhao, Jiangsu (CN); Jie Li, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 642 days.

(21) Appl. No.: 18/039,286

(22) PCT Filed: Nov. 7, 2022

(86) PCT No.: PCT/CN2022/130220
§ 371 (c)(1),
(2) Date: May 30, 2023

(87) PCT Pub. No.: WO2024/021359
PCT Pub. Date: Feb. 1, 2024

(65) Prior Publication Data
US 2024/0335156 A1 Oct. 10, 2024

(30) Foreign Application Priority Data
Jul. 27, 2022 (CN) .......................... 202210896092.0

(51) Int. Cl.
*A61B 5/372* (2021.01)
*A61B 5/00* (2006.01)
(Continued)

(52) U.S. Cl.
CPC ............ *A61B 5/372* (2021.01); *A61B 5/7257* (2013.01); *G06T 7/11* (2017.01); *G06T 7/90* (2017.01);
(Continued)

(58) Field of Classification Search
CPC ..... A61B 5/372; A61B 5/7257; A61B 5/7267; G06T 7/11; G06T 7/90;
(Continued)

(56) References Cited

U.S. PATENT DOCUMENTS

2024/0013925 A1* 1/2024 Bukowski .............. G16H 50/30

FOREIGN PATENT DOCUMENTS

CN 110135244 8/2019
CN 110751362 2/2020
(Continued)

OTHER PUBLICATIONS

Zhang Z, Zhuo K, Wei W, Li F, Yin J, Xu L. Emotional Responses to the Visual Patterns of Urban Streets: Evidence from Physiological and Subjective Indicators. Int J Environ Res Public Health. Sep. 14, 2021;18(18):9677. doi: 10.3390/ijerph18189677. PMID: 34574601; PMCID: PMC8467209. (Year: 2021).*
(Continued)

*Primary Examiner* — Matthew C Bella
*Assistant Examiner* — Shane Wrensford Codrington
(74) *Attorney, Agent, or Firm* — JCIPRNET

(57) ABSTRACT

The present disclosure provides a measurement method and system based on image electroencephalogram sensitivity data for a built environment dominant color, and relates to the field of urban quality measurement. The measurement
(Continued)

method based on image electroencephalogram sensitivity data for a built environment dominant color includes acquiring electroencephalogram data corresponding to a built environment image sample; calculating an environment dominant color sensitivity on the basis of the electroencephalogram data; extracting a dominant color feature parameter according to the built environment image sample; constructing a built environment dominant color measurement model, and training same by taking sensitivity data and a dominant color feature as an input; and inputting an environment image to be analyzed into a trained model, so as to obtain a predicted dominant color sensitivity result. Therefore, the problems that a prediction effect of a nonlinear model integrating an image color feature and an environment quality is improved.

7 Claims, 6 Drawing Sheets

(51) Int. Cl.
| | |
|---|---|
| *G06T 7/11* | (2017.01) |
| *G06T 7/90* | (2017.01) |
| *G06V 10/56* | (2022.01) |
| *G06V 10/762* | (2022.01) |
| *G06V 10/774* | (2022.01) |
| *G06V 10/776* | (2022.01) |

(52) U.S. Cl.
CPC ............ *G06V 10/56* (2022.01); *G06V 10/762* (2022.01); *G06T 2207/10024* (2013.01)

(58) Field of Classification Search
CPC . G06T 2207/10024; G06T 2207/20081; G06T 2207/30184; G06V 10/56; G06V 10/762; G06V 10/776; G06V 10/774
See application file for complete search history.

(56) References Cited

FOREIGN PATENT DOCUMENTS

| | | |
|---|---|---|
| CN | 113610293 | 11/2021 |
| CN | 113673456 | 11/2021 |
| CN | 115063653 | 9/2022 |
| WO | 2016192552 | 12/2016 |

OTHER PUBLICATIONS

Xing, Baixi & Zhang, Hui & Zhang, Kejun & Zhang, Lk & Wu, Xinda & Shi, Xiaoying & Yu, Shanghai & Zhang, Sanyuan. (2019). Exploiting EEG Signals and Audiovisual Feature Fusion for Video Emotion Recognition. IEEE Access. pp. 1-1. 10.1109/ACCESS. 2019.2914872. (Year: 2019).*
Ghebreab, Sennay & Scholte, H. & Lamme, Victor & Smeulders, A.W.M.. (2009). A biologically plausible model for rapid natural scene identification. Advances in Neural Information Processing Systems (NIPS). 1-9. (Year: 2009).*
"International Search Report (Form PCT/ISA/210) of PCT/CN2022/ 130220," mailed on Apr. 4, 2023, pp. 1-3.
"Written Opinion of the International Searching Authority (Form PCT/ISA/237) of PCT/ CN2022/130220," mailed on Apr. 4, 2023, pp. 1-5.
Li Zhe et al., "The Principal Component Quantitative Analysis of Landscape Attraction Based on the EEG Technology—Taking Xuanwu Lake Park of Nanjing as the Example," China Garden Magazine Co., Ltd, vol. 37, May 2021, pp. 60-65.
Li Zhe et al., "Quantitative Research on Landscape Emotion Based on Scenescape Electroencephalogram GRA-TOPSIS Model: A Case Study of Xiangyang Weidong Plant," Landscape Architecture, Jul. 2022, pp. 33-40.

* cited by examiner

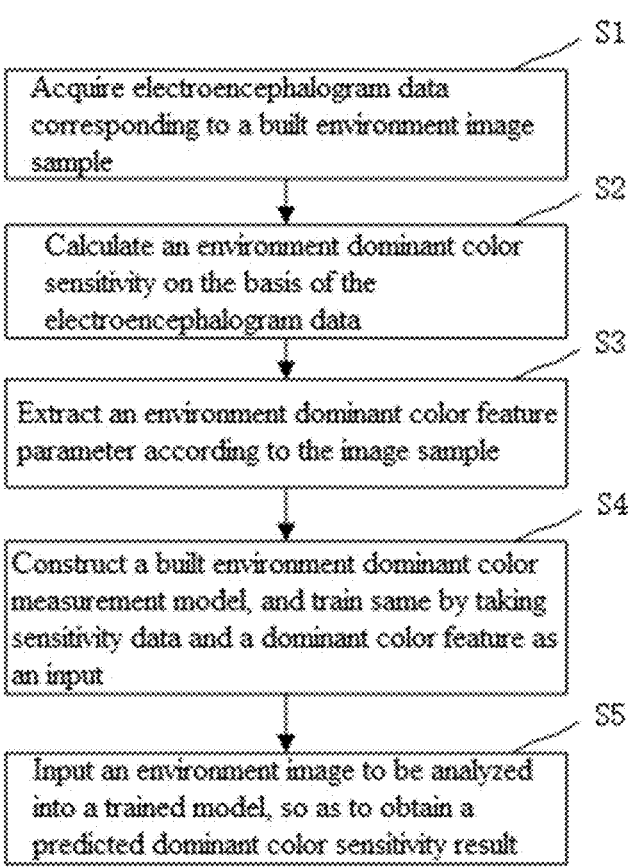

S1
Acquire electroencephalogram data corresponding to a built environment image sample S2
Calculate an environment dominant color sensitivity on the basis of the electroencephalogram data S3
Extract an environment dominant color feature parameter according to the image sample S4
Construct a built environment dominant color measurement model, and train same by taking sensitivity data and a dominant color feature as an input S5
Input an environment image to be analyzed into a trained model, so as to obtain a predicted dominant color sensitivity result

FIG. 1

MEASUREMENT METHOD AND SYSTEM BASED ON IMAGE ELECTROENCEPHALOGRAM SENSITIVITY DATA FOR BUILT ENVIRONMENT DOMINANT COLOR

CROSS-REFERENCE TO RELATED APPLICATION

This application is a 371 of international application of PCT application serial no. PCT/CN2022/130220, filed on Nov. 7, 2022, which claims the priority benefit of China application serial no. 202210896092.0, filed on Jul. 7, 2022. The entirety of each of the above-mentioned patent applications is hereby incorporated by reference herein and made a part of this specification.

TECHNICAL FIELD

The present disclosure relates to the technical field of urban quality measurement, and in particular to a measurement method and system based on image electroencephalogram sensitivity data for a built environment dominant color.

BACKGROUND ART

Typically, a built environment dominant color, crucial to an environment quality, can be an effective index of a built environment order and function. It is thus believed to have a vital impact on regional location and spatial organization, attempting to improve an environment quality and efficiency. The perceptible and identifiable environment dominant color can be effectively applied to urban quality measurement. For example, in view of urban renewal and protection, a chaotic urban color status is measured and diminished by optimizing a built environment dominant color system, so as to invest an old city with a unified and coordinated dominant color style. In view of environment planning and design, color design problems are adjusted in time after an environment standard color is constructed through environment dominant color quality measurement. Accordingly, built environment planning and management are improved.

In recent years, in order to improve an environment quality evaluation effect of the environment dominant color, it is increasingly common practice for scholars to associate image data with dominant color analysis and prediction. The relevant intellectual property achievements are as follows: for example, Patent Application No. CN202110987218.0 and entitled "STREET VIEW IMAGE SCORING METHOD BASED ON COLOR DISTRIBUTION LEARNING", which describes a street view image scoring method based on machine learning and color distribution derived through image semantic segmentation, image entity color value calculation, entity mixed color evaluation, and label data training; Patent Application No. CN202110893036.7 and entitled "METHOD AND DEVICE FOR EVALUATING COLOR HARMONY DEGREE OF URBAN BLOCK BUILDING", which describes a method for evaluating a color harmony degree of an urban block building derived through building photo sample acquisition, photo color extraction and analysis, color region division, and attractiveness evaluation; and Patent Application No. CN201910833403.7 and entitled "URBAN LANDSCAPE EVALUATION INDEX CALCU-LATION METHOD BASED ON ARTIFICIAL INTELLI-GENCE ALGORITHM", which describes a color landscape evaluation index calculation method derived through influence factor weight construction, urban evaluation picture set collection, a landscape color richness score, and a factor target evaluation function. Although some progress has been made in the research of environment dominant color measurement methods based on image data, a prediction effect of a nonlinear model integrating a multi-dimensional image dominant color feature and an environment quality remains to be further improved. Moreover, a conventional environment image evaluation features a complicated process, an extreme long overall flow cycle, and a high labor cost in environment dominant color quality identification. Accordingly, dominant color information can hardly be fed back synchronously, affecting the accuracy and efficiency of environment dominant color quality prediction.

Therefore, during environment dominant color measurement and analysis, a method in the prior art has the disadvantages of subjectivity and randomness of basic data processing and analysis, and an operation efficiency, precision, and comprehensiveness of a measurement model far from perfectness, for example. It is impossible to employ such a method in complex built environment dominant color measurement research and in-depth guide of built environment landscape dominant color quality analysis. A built environment dominant color measurement method combined with image electroencephalogram sensitivity data is to be optimized, developed, and applied immediately. Accordingly, the built environment dominant color and environment quality measurement is analyzed precisely, multi-dimensionally, and overally, thereby boosting the improvement in urban quality and efficiency.

SUMMARY

1. Technical Problem to be Solved

In view of the shortcomings in the prior art, the present disclosure provides a measurement method and system based on image electroencephalogram sensitivity data for a built environment dominant color. Therefore, the problems that a prediction effect of a nonlinear model integrating a multi-dimensional image color feature and an environment quality remains to be improved; and moreover, a conventional environment image evaluation features a complicated process and an extreme long overall flow cycle, and accordingly, dominant color information can hardly be fed back synchronously, affecting the accuracy and efficiency of environment dominant color quality prediction are solved.

2. Technical Solution

In order to realize the above objective, the present disclosure employs the technical solutions as follows:

In one aspect, a measurement method based on image electroencephalogram sensitivity data for a built environment dominant color is provided. The method includes:

acquiring electroencephalogram data corresponding to a built environment image sample;

calculating an environment dominant color sensitivity on the basis of the electroencephalogram data;

extracting a dominant color feature parameter according to the built environment image sample;

constructing a built environment dominant color measurement model, and training same by taking sensitivity data and a dominant color feature as an input; and inputting an environment image to be analyzed into a trained model, so as to obtain a predicted dominant color sensitivity result.

Preferably, the acquiring electroencephalogram data corresponding to a built environment image sample includes: collecting electroencephalogram data of J subjects on I built environment image samples under the same laboratory environment to obtain I*J electroencephalogram data groups, where a data size of each data group is $n^{(d)}$, d denotes a dominant color feature dimension of each data group, and n denotes the number of an electroencephalogram data sample collected at a time.

Preferably, the calculating an environment dominant color sensitivity on the basis of the electroencephalogram data specifically includes:

selecting electroencephalogram signals, generated within 3 seconds before and after stimulation of the built environment image sample, of eight leads of occipital lobe regions O1, OZ, O2, POZ, PO3, PO4, PO7, and PO8;

acquiring difference wave data before and after sample visual stimulation through original electroencephalogram data;

performing short-time Fourier transform on an electroencephalogram signal of each lead, and extracting power spectral densities of frequency band $\alpha$ of 8 Hz-13 Hz, frequency band $\beta$ of 14 Hz-41 Hz, and frequency band $\theta$ of 4 Hz-8 Hz of pre-processed electroencephalogram data, respectively;

calculating an electroencephalogram sensitivity index according to average relative power spectra of frequency bands $\alpha$, $\beta$, and $\theta$, so as to obtain a built environment dominant color sensitivity of the image sample, a calculation process of which is as follows:

$$E_{FT} = \frac{1}{8} \sum_k \frac{P_\theta(k) + P_a(k)}{P_\beta(k)}$$

where $E_{FT}$ denotes the electroencephalogram sensitivity index, $1 \leq k \leq 8$ denoting the eight leads, and $P_\theta(k)$, $P_\alpha(k)$, and $P_\beta(k)$ denote the average relative power spectra of frequency bands $\alpha$, $\beta$, and $\theta$ of the lead, respectively; and nondimensionalizing the electroencephalogram sensitivity index according to an influence from an individual difference of the subject, which is specifically as follows:

$$Z_j(i) = z_j(i) / \frac{1}{n} \sum_{i=1}^{n} z_j(i)$$

where $Z_j(i)$ denotes a nondimensionalized electroencephalogram sensitivity of a $j^{th}$ subject on an $i^{th}$ image sample, and n denotes the number of the image sample; where a built environment dominant color sensitivity value is as follows:

$$E_{AT} = \frac{1}{Z_j(i)} * 100\%.$$

Preferably, the extracting a dominant color feature parameter according to the built environment image sample specifically includes:

performing data dimension conversion on a sample image $\{i_1, i_2, \ldots, i_m\}$ to set a size of a zoomed image to 1024 pixels×600 pixels;

identifying and segmenting a color of the image, and outputting color cluster division $D = \{d_1, d_2, \ldots, d_k\}$, which is specifically as follows:

$$S = \sum_{n=1}^{N} \sum_{k=1}^{K} r_{nk} \|Q(n) - d_k\|^2$$

$$d_k = \frac{1}{T_k} \sum_{i=1}^{T_k} Q(n)$$

where S denotes the sum of distortion degrees of all color clusters, Q(n) denotes a color value of the pixel, N denotes the number of a pixel of the color cluster, n denotes coordinates of a pixel point of an environment image, $d_k$ denotes a centroid of a color of type k, K denotes the number of the color cluster, $r_{nk}$ denotes two components configured to determine whether Q(n) belongs to the color of type k, and $T_k$ denotes the number of a pixel of a $k^{th}$ color cluster;

acquiring all color names associated with an image color cluster according to an image sample color extraction result, and calculating saturation, lightness, brightness, a channel of a $\{k_1, k_2, \ldots, k_j\}$th color type of the image sample, and an area and a perimeter of a color cluster block, where a boundary of the color cluster block is calculated on the basis of an average of a pixel color and smoothed moderately to avoid a measurement error caused by simplifying the boundary;

constructing the environment dominant color feature parameter including a hue proportion, a saturation proportion, a lightness proportion, a maximum color cluster area, color cluster shape complexity, color cluster diversity, a color cluster segmentation degree, and a similar color cluster spread degree; and performing min-max normalization processing on an environment dominant color feature, which is specifically as follows:

$$H_{std} = \frac{H_{int} - \min(H_{int})}{\max(H_{int}) - \min(H_{int})}$$

where $H_{std}$ denotes a feature value before normalization, and $H_{int}$ denotes a result of a normalized feature value.

Preferably, the constructing a built environment dominant color measurement model, and training same by taking sensitivity data and a dominant color feature as an input specifically includes:

converting the built environment image and electroencephalogram sensitivity data thereof into several build environment sequence samples, constructing the built environment dominant color measurement model through an XGBoost decision tree algorithm, training 75% of built environment sample data, and taking remaining sample data as a test set;

fusing environment dominant color features of eight dimensions through a concat method to obtain an overall environment dominant color feature $H_{all}$;

inputting the sensitivity data and the dominant color feature parameter into the built environment dominant color measurement model, which is specifically as follows:

$$Z=\{(H_i,y_i)|i=1,2,\ldots,n\}$$

where $H_i$ denotes an overall environment dominant color feature of an $i^{th}$ image sample, $y_i$ denotes a dominant color sensitivity value of the image sample, and n denotes the number of the image sample; and performing a Kaiser-Meyer-Olkin test and a Bartlett's test of sphericity on an input feature parameter.

Preferably, the inputting an environment image to be analyzed into a trained model, so as to obtain a predicted dominant color sensitivity result specifically includes:

acquiring a nonlinear regression model for predicting the built environment dominant color as follows by taking the hue proportion (HS), the saturation proportion (BS), the lightness proportion (VS), the maximum color cluster area (MCA), the color cluster diversity (NPC), the color cluster shape complexity (CDS), the color cluster segmentation degree (DPS), and the similar color cluster spread degree (IPS) as influence indexes:

$$Prec_{XGBoost}=f_{XGBoost}(HS,BS,VS,MCA,NPC,CDS,DPC,IPS)$$

where $Prec_{XGBoost}$ denotes predicted dominant color sensitivity data, $Prec_{XGBoost}\ \varepsilon(0,100]$;

applying a loss function as follows, so as to make a finally-trained weight smoother, thereby avoiding an overfitting phenomenon:

$$L(\varphi) = \sum_i l(y_i, \hat{y}_i) + \sum_m \left(\eta T + \frac{1}{2}\rho\|\omega\|^2\right) + c$$

where $L(\varphi)$ denotes a set of differences between all predicted parameters and an actual parameter of a model regression tree, $l(y_i,\hat{y}_i)$ denotes a difference between a predicted measurement parameter and a target parameter, $$\eta T + \frac{1}{2}\rho\|\omega\|^2$$

denotes a regularization term optimization function for avoiding overfitting. T denotes the number of a leaf node of the regression tree, $\omega$ denotes a score of each leaf node, and $\eta$ and $\rho$ denote coefficients with parameters to be adjusted;

calculating a dominant color feature importance score of the model, which is specifically as follows:

$$F(i) = \frac{\left(\overline{x}_i^{(+)} - \overline{x}_i\right)^2 + \left(\overline{x}_i^{(-)} - \overline{x}_i\right)^2}{\frac{1}{n_+ - 1}\sum_{r=1}^{n_+}\left(x_{r,i}^{(+)} - \overline{x}_i^{(+)}\right)^2 + \frac{1}{n_- - 1}\sum_{r=1}^{n_-}\left(x_{r,i}^{(-)} - \overline{x}_i^{(-)}\right)^2}$$

where $\overline{x}_i$ denotes an average of an $i^{th}$ dominant color feature value of the sequence sample, $$\overline{x}_i^{(+)}\ \text{and}\ \overline{x}_i^{(-)}$$

denote averages of feature values of all positive samples and all negative samples, respectively, and r denotes an instance corresponding to an $i^{th}$ environment dominant color feature; and the greater the F(i) is, the greater the feature influence on the dominant color sensitivity, so that a crucial landscape color feature may be screened, and an environment dominant color quantification system may be constructed comprehensively, thereby improving an environment planning and design quality; and calculating a dominant color feature weight of the model, and evaluating an environment dominant color quality according to the feature weight, a specific processing process of which is as follows:

$$w_t^* = \frac{-\sum_{i=1}^{n}G_i}{\sum_{i=1}^{n}H_i + \lambda}$$

where $$w_t^*$$

denotes a weight value of a $i^{th}$ environment dominant color feature of the built environment sequence sample, $$\sum_{i=1}^{n}G_i$$

denotes the sum of gradient statistics of all leaf samples of the model regression tree, and $$\sum_{i=1}^{n}H_i + \lambda$$

denotes the sum of second order statistics of all the leaf samples of the model regression tree; where a calculation formula of an environment dominant color quality score is as follows:

$$H_{quality} =$$
$$n \cdot w_1 H_1 + 5 \cdot w_2 H_2 + 4 \cdot w_3 H_3 + w_4 H_4 + w_5 H_5 + + w_6 H_6 + w_7 H_7 + w_8 H_8$$

where n denotes the total number of a hue of the color cluster, w denotes the weight value of the dominant color feature, H denotes the dominant color feature parameter, and a final environment dominant color quality score is acquired by normalizing $H_{quality}$.

In another aspect, a measurement system based on image electroencephalogram sensitivity data for a built environment dominant color is provided. The system includes:

a data collection processing module configured to acquire several built environment images and electroencephalogram data corresponding thereto, and convert same into several build environment image sequence samples;

an electroencephalogram sensitivity extraction module configured to extract an electroencephalogram sensitivity index from the electroencephalogram data, so as to obtain a built environment dominant color sensitivity value;

a dominant color feature extraction module configured to identify and segment an image color from an image sample, so as to obtain an image color cluster and a dominant color feature parameter;

an environment dominant color measurement model training module configured to construct a built environment dominant color measurement model, input sensitivity data and the dominant color feature parameter, and train the model through an XGBoost decision tree algorithm;

a feature importance identification module configured to identify an important dominant color feature, and construct a comprehensive environment dominant color measurement system according to an environment dominant color feature selection table; and a quality quantitative evaluation module applied to a built environment measurement method and configured to evaluate an environment dominant color quality according to a dominant color feature weight.

Preferably, the electroencephalogram sensitivity extraction module specifically includes:

an electroencephalogram signal pre-processing unit configured to perform filtering and artifact correction on original electroencephalogram data, remove data with amplitudes beyond an interval range of 10 μV-100 μV as a bad lead, and perform re-classification and superposed averaging according to the image sample;

an electroencephalogram frequency band extraction unit configured to extract average relative power spectra of frequency bands α, β, and θ of eight leads;

a sensitivity index calculation unit configured to calculate an electroencephalogram sensitivity index from an electroencephalogram feature; and a dominant color sensitivity acquisition unit configured to acquire a built environment dominant color sensitivity value as training data of the environment dominant color measurement model.

The dominant color feature extraction module includes:

a sample image processing unit configured to perform data dimension conversion on the image sequence sample;

a color cluster extraction unit configured to identify and segment a color of the image sequence sample, so as to obtain saturation, lightness, brightness, and a channel of the image sample, and an area and a perimeter of a color cluster block;

a dominant color feature selection unit configured to construct an environment dominant color feature including a hue proportion, a saturation proportion, a lightness proportion, a maximum color cluster area, color cluster shape complexity, color cluster diversity, a color cluster segmentation degree, and a similar color cluster spread degree;

a feature parameter calculation unit configured to calculate each dominant color feature parameter; and a normalization unit configured to encode the dominant color feature as an input feature of the built environment dominant color measurement model, so that the environment dominant color feature parameter falls within an interval [0,1].

The environment dominant color measurement model training module specifically includes:

an environment dominant color measurement model construction unit configured to construct an environment dominant color sensitivity and dominant color feature measurement model through an XGBoost decision tree algorithm;

a feature fusion unit configured to accelerate a training process;

an environment dominant color measurement model training unit configured to train a nonlinear regression model taking an environment dominant color feature as an influence index; and an environment dominant color sensitivity prediction unit configured to input built environment image data to be predicted into a trained environment dominant color measurement model, so as to obtain a predicted built environment dominant color sensitivity.

BRIEF DESCRIPTION OF THE DRAWINGS

FIG. 1 is a flowchart of a measurement method based on image electroencephalogram sensitivity data for a built environment dominant color according to the present disclosure;

DETAILED DESCRIPTION OF THE EMBODIMENTS

The technical solutions in the examples of the present disclosure are clearly and completely described below with reference to the accompanying drawings of the present disclosure. Apparently, the described examples are some examples rather than all examples of the present disclosure. Based on the examples of the present disclosure, all other examples derived by those of ordinary skill in the art without making creative efforts fall within the scope of protection of the present disclosure.

Example 1

As shown in FIG. 1, the present example provides a measurement method based on image electroencephalogram sensitivity data for a built environment dominant color. The method specifically includes:

Electroencephalogram data corresponding to a built environment image sample are acquired. Electroencephalogram data of J subjects on I built environment image samples under the same laboratory environment are collected to obtain I*J electroencephalogram data groups, where a data size of each data group is $n^{(d)}$, d denotes a dominant color feature dimension of each data group, and n denotes the number of an electroencephalogram data sample collected at a time.

In the present example, all subjects are selected according to ages at a certain sex ratio. They have the healthy physiological and psychological states and similar living environments, and have signed the informed consent form. A visual stimulation presentation and electroencephalogram data collection system is constructed through an E-Prime experimental operation system. Each environment image is displayed three times (3 seconds per time). Therefore, original electroencephalogram signals of the subjects are collected in real time.

Figure 2:
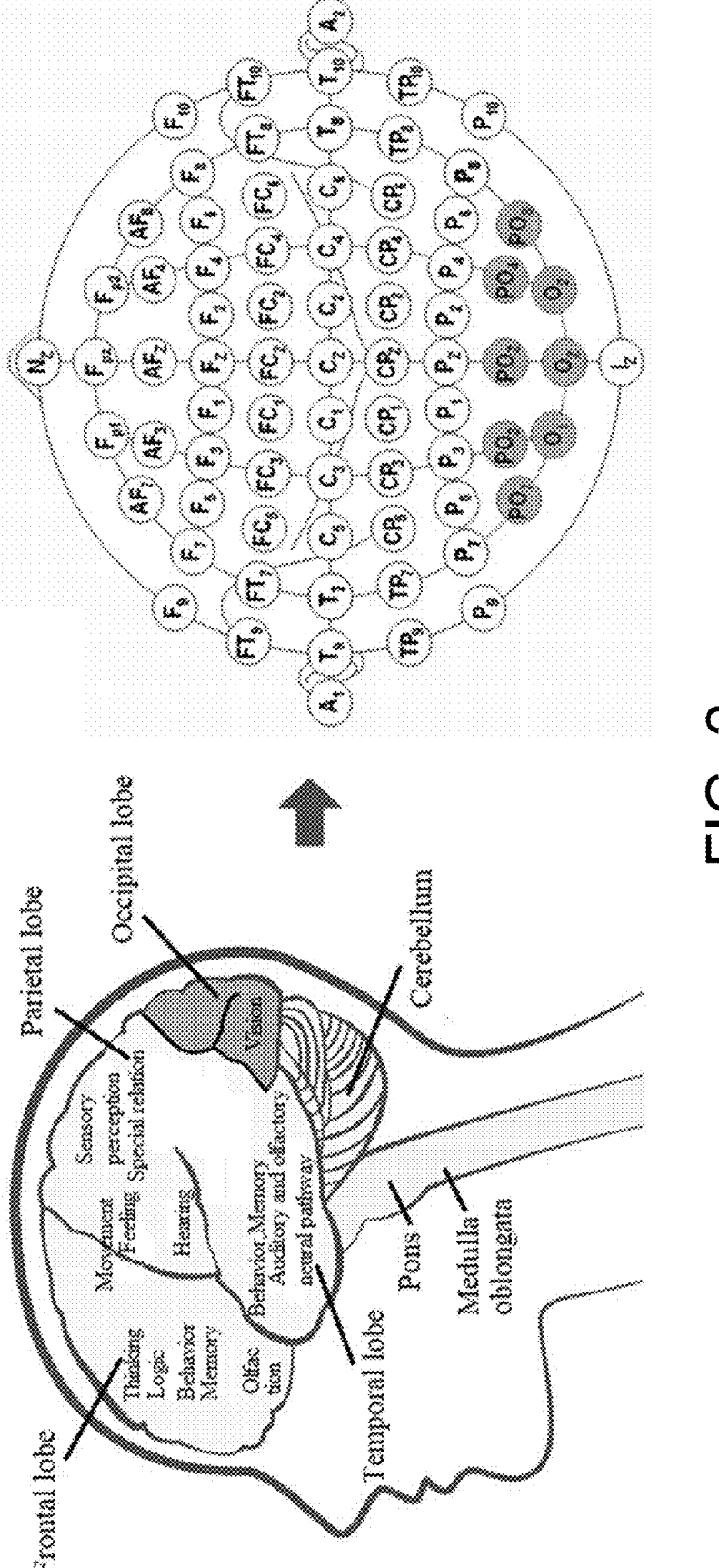
FIG. 2 is a schematic diagram of collection lead electrodes in a visual region and an occipital lobe region of a brain according to an example of the present disclosure.

An environment dominant color sensitivity is calculated on the basis of the electroencephalogram data, which specifically includes:

electroencephalogram signals, generated within 3 seconds before and after stimulation of the built environment image sample, of eight leads (as shown in FIG. 2) of occipital lobe regions O1, OZ, O2, POZ, PO3, PO4, PO7, and PO8 are selected, where the electroencephalogram signal of the lead of the region may better reflect visual information of an environment color; it should be noted that the left hemisphere of the parietal lobe controls speech, movement and feeling, while the right hemisphere of the parietal lobe controls abstraction and concept.

in order to increase an electroencephalogram feature extraction speed and reduce redundant calculation, original electroencephalogram data undergo electrode locating, filtering, independent component analysis, artifact removal, baseline calibration, and re-classification processing to obtain a difference wave of sample visual stimulation data, where a difference wave amplitude denotes an influence of the image sample on an electroencephalogram sensitivity of a human being;

short-time Fourier transform is performed on an electroencephalogram signal of each lead, window processing is performed through a hanning window, and power spectral densities of frequency band α (8 Hz-13 Hz), frequency band β (14 Hz-41 Hz), and frequency band θ (4 Hz-8 Hz) of pre-processed electroencephalogram data are extracted, respectively;

an electroencephalogram sensitivity index (FTG) is calculated according to average relative power spectra of frequency bands α, β, and θ, so as to obtain a built environment dominant color sensitivity (ATD) of the image sample, a calculation process of which is as follows:

$$E_{FT} = \frac{1}{8} \sum_k \frac{P_\theta(k) + P_a(k)}{P_\beta(k)}$$

where $E_{FT}$ denotes the electroencephalogram sensitivity index, $1 \le k \le 8$ denoting the eight leads, and $P_\theta(k)$, $P_\alpha(k)$, and $P_\beta(k)$ denote the average relative power spectra of frequency bands α, β, and θ of the lead, respectively; and an electroencephalogram sensitivity index is nondimensionalized according to an influence from an individual difference of the subject, which is specifically as follows:

$$Z_j(i) = z_j(i) / \frac{1}{n} \sum_{j=1}^{n} z_j(i)$$

where $Z_j(i)$ denotes a nondimensionalized electroencephalogram sensitivity of a $j^{th}$ subject on an $i^{th}$ image sample, and n denotes the number of the image sample; where a built environment dominant color sensitivity value is as follows:

$$E_{AT} = \frac{1}{Z_j(i)} * 100\%$$

where the dominant color sensitivity is configured to measure a built environment dominant color quality. When the sensitivity value $E_{AT}$ is ≥60, an influence of the dominant color sensitivity is deemed great. When $40 \le E_{AT} < 60$, an influence of the dominant color sensitivity is deemed moderate. When $0 < E_{AT} < 40$, an influence of the dominant color sensitivity is deemed slight.

Figure 3:
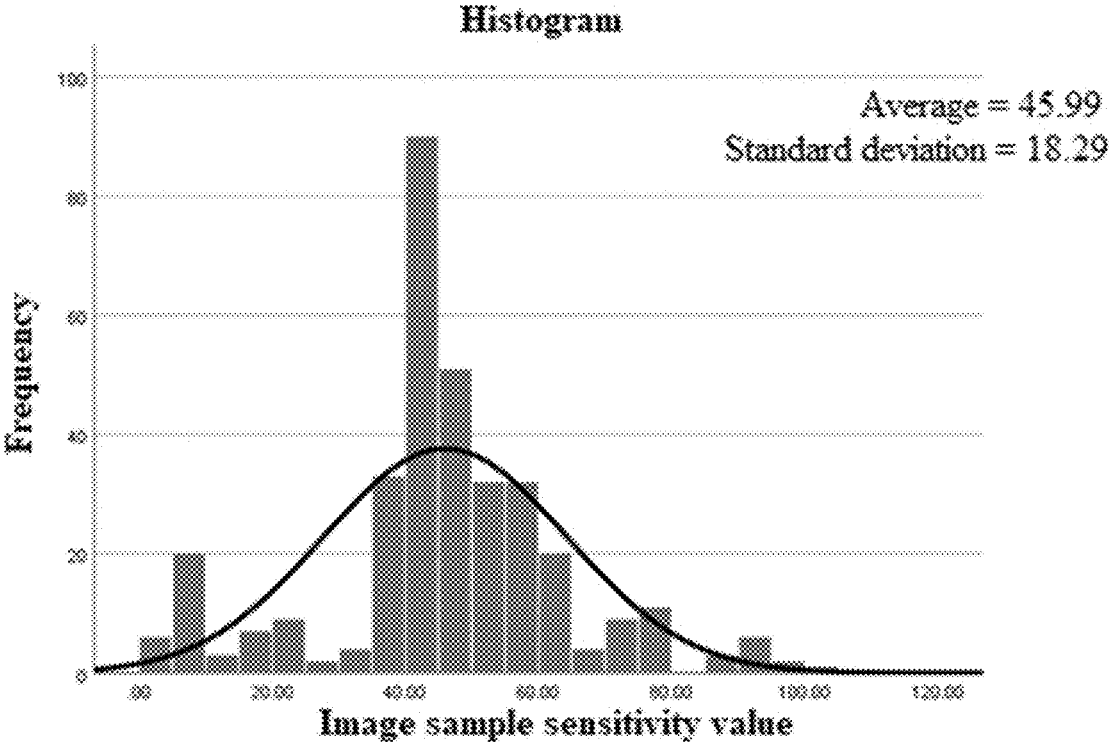
FIG. 3 is a distribution graph of an electroencephalogram sensitivity of a built environment image sample according to an example of the present disclosure.
Figure 4:
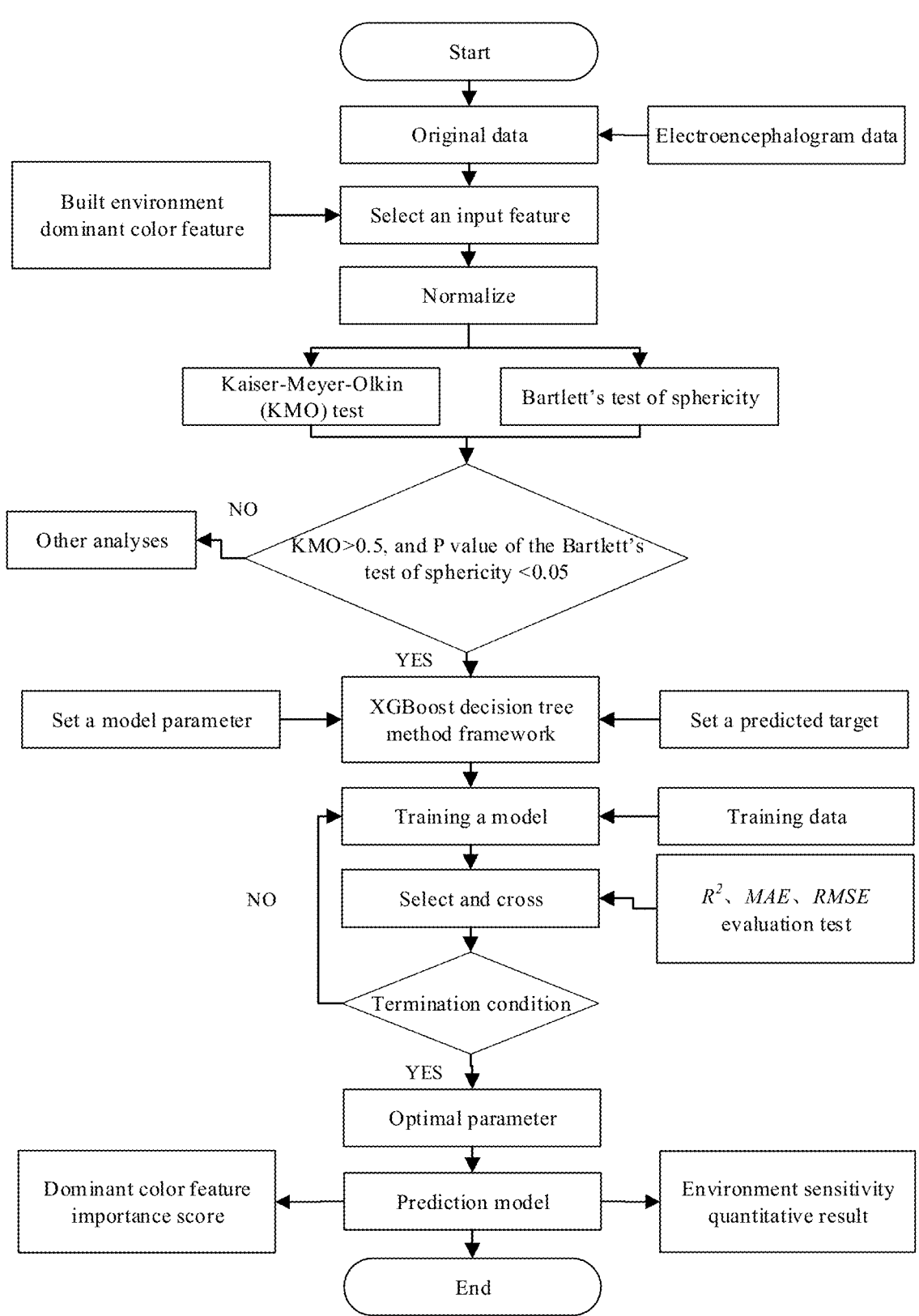
FIG. 4 is a flowchart of an XGBoost decision tree method according to an example of the present disclosure.

In the example, original electroencephalogram data pre-processing and frequency band extraction are performed through an adaptive security appliance (asa) analysis software package of eegmylab. The software features a high electroencephalogram filtering and artifact correcting speed. After a required lead electrode position is introduced, and an average electrode reference is employed, data with amplitudes beyond an interval range of 10 μV-100 μV are removed as bad leads. Therefore, the artifact interference of an electrooculogram and an electromyogram is removed. Re-classification and superimposed averaging are performed according to the image sample, and then an amplitude and a phase of the data are analyzed. The average relative power spectra of frequency bands α, β, and θ are grabbed. Finally, the dominant color sensitivity value (as shown in FIG. 3) of the built environment image sample is acquired.

A dominant color feature parameter is extracted according to the built environment image sample, which specifically includes:

data dimension conversion is performed on an image sample $\{i_1, i_2, \ldots, i_m\}$ to set a size of a zoomed image to 1024 pixels×600 pixels;

a color of the image is identified and segmented, and color cluster division $D = \{d_1, d_2, \ldots, d_k\}$ is output, which is specifically as follows:

$$S = \sum_{n=1}^{N} \sum_{k=1}^{K} r_{nk} \|Q(n) - d_k\|^2$$

$$d_k = \frac{1}{T_k} \sum_{i=1}^{T_k} Q(n)$$

where S denotes the sum of distortion degrees of all color clusters, Q(n) denotes a color value of the pixel, N denotes the number of a pixel of the color cluster, n denotes coordinates of a pixel point of an environment image, $d_k$ denotes a centroid of a color of type k, K denotes the number of the color cluster, $r_{nk}$ denotes two components configured to determine whether Q(n) belongs to the color of type k, and $T_k$ denotes the number of a pixel of a $k^{th}$ color cluster;

all color names associated with an image color cluster are acquired according to an image sample color extraction result, and saturation, lightness, brightness, a channel of a $\{k_1, k_2, \ldots, k_j\}$ th color type of the image sample, and an area and a perimeter of a color cluster block are calculated, where a boundary of the color cluster block is calculated on the basis of an average of a pixel color and smoothed moderately to avoid a measurement error caused by simplifying the boundary;

the environment dominant color feature parameter (Table 1) is constructed, including a hue proportion, a saturation proportion, a lightness proportion, a maximum color cluster area, color cluster shape complexity, color cluster diversity, a color cluster segmentation degree, and a similar color cluster spread degree; and

TABLE 1

| Environment dominant color feature selection | | | |
|---|---|---|---|
| Name | Abbreviation | Function | Formula |
| Hue proportion | HS | describe a proportion of an image color | $C_{HS,i} = \dfrac{f(E_n)}{N}$, |
| | | cluster to n hues $\{E_1, E_2, \ldots, E_n\}$, $E \in (15, 345]$ | where $C_{HS,i}$ denotes a hue proportion of an i th image, $E_n$ denotes the total number of pixels occupied by a hue of type n, and N denotes the total number of pixels of the image |
| Saturation proportion | BS | describe a proportion of an image color | $C_{BS,i} = \dfrac{f(S_n)}{N}$, |
| | | cluster to five saturation type intervals of $S_1$, $S_2$, $S_3$, white, and gray, $S \in (0, 1]$ | where $C_{BS,i}$ denotes a saturation proportion of an $i^{th}$ image, $S_n$ denotes the total number of pixels occupied by a saturation interval of type n , and N denotes the total number of pixels of the image |
| Lightness proportion | VS | describe a proportion of an image color | $C_{VS,i} = \dfrac{f(V_n)}{N}$, |
| | | cluster to four lightness type intervals of $V_1$, $V_2$, $V_3$, and black, $V \in (0, 1]$ | where $C_{VS,i}$ denotes a lightness proportion of an $i^{th}$ image, $V_n$ denotes the total number of pixels occupied by a lightness interval of type n, and N denotes the total number of pixels of the image |
| Maximum color | MCA | describe a color cluster pixel color | $C_{MC,i} = \dfrac{f(M_n)}{N}$, |
| cluster area | | block with a largest proportion in an image | where $C_{MC,i}$ denotes a maximum color cluster area of an $i^{th}$ image, $M_n$ denotes the total number of pixels of a color cluster with a maximum proportion, and N denotes the total number of pixels of a landscape image |
| Color cluster diversity | NPC | describe uniformity of a color cluster, the greater the diversity | $C_{NP,i} = \displaystyle\sum_{i=1}^{m} (p_j \ln p_j)$, |
| | | value is, the higher the uniformity is | where $_{CNP,i}$ denotes color cluster diversity of an $i^{th}$ image, m denotes the number of a color cluster, and $p_j$ denotes a proportion of pixels of a color cluster of type j in the image |
| Color cluster | CDS | describe average complexity of a color | $C_{CD,i} = \dfrac{2\lg(0.25P_j)}{\lg(A_j)}$, |
| shape complexity | | cluster shape in an image, the greater the CDS is, the more complex the color cluster shape is | where $C_{CD,i}$ denotes color cluster shape complexity of an $i^{th}$ image, and $P_j$ and $A_j$ denote a perimeter and an area of a color cluster pixel color block of type j of the image, respectively |
| Color cluster segmentation | DPS | describe a fragmentation degree of a segmented color | $C_{DP,s} = 1 - \displaystyle\sum_{i=1}^{m}\sum_{j=1}^{n}\left(\dfrac{t_{ij}}{A}\right)^2$, |
| degree | | cluster pixel color block in an image, the greater the DPS is, the more complex the spatial structure of a color cluster is, and the higher the overall heterogeneity is | where $C_{DP,s}$ denotes a color cluster segmentation degree of an s th image, m denotes the number of a color cluster, n denotes the total number of a certain color cluster block, $t_{ij}$ denotes an area of a $j^{th}$ color cluster block of a color cluster of type i , and A |

TABLE 1-continued

| Environment dominant color feature selection | | | |
| --- | --- | --- | --- |
| Name | Abbreviation | Function | Formula |
| | | | denotes a total area of color clusters in the image |
| Similar color cluster spread degree | IPS | describe a convergence condition of color clusters in an image, the greater the IPS is, | $C_{IP,s} = \dfrac{-\sum\limits_{i=1}^{m} a \ln a}{\ln(m-1)},$ |
| | | the better the continuity of the color clusters is, and when | where $C_{IP,s}$ denotes a similar color cluster spread degree of an s th image, |
| | | IPS = 1, it indicates that probabilities that the color clusters are | $a = l_{ik} / \sum\limits_{i=1}^{m} l_{ik}$ |
| | | adjacent to each other are the same | denotes a length variable of a boundary between color clusters i and k, and m denotes the number of color clusters | min-max normalization processing is performed on an environment dominant color feature, which is specifically as follows:

$$H_{std} = \frac{H_{int} - \min\,(H_{int})}{\max\,(H_{int}) - \min\,(H_{int})}$$

where $H_{std}$ denotes a feature value before normalization, and $H_{int}$ denotes a result of a normalized feature value.

In the present example, K is set to [4, 6], so as to obtain a color cluster (as shown in FIG. 3) close to a visual space of a human being, that is, a dominant color of the image sample. The sum of squared errors (SSE) is taken as an evaluation index. The smaller the SSE is, the closer the data point is to a centroid of the color cluster, that is, the better the sample color extraction effect is. The color cluster saturation and lightness are calculated through an open source histogram estimator cv2.calcHist of OpenCV. The area and perimeter of the color cluster pixel color block are calculated through a Canny edge detector, so as to calculate an environment dominant color feature parameter of each image. The environment dominant color feature parameters fall within an interval [0, 1] through normalization processing, and may be encoded as input features of a built environment dominant color measurement model.

Figure 5:
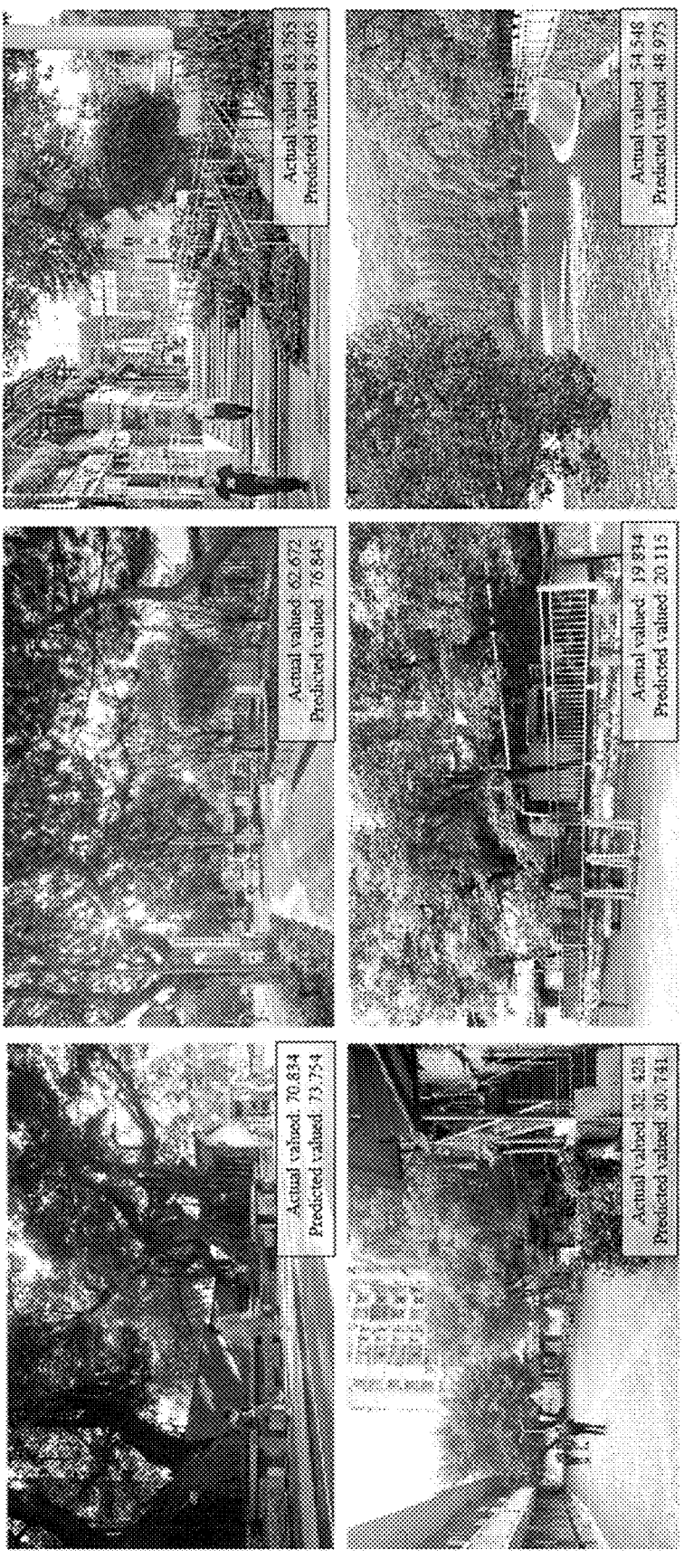
FIG. 5 is a schematic diagram of a predicted result of a built environment dominant color measurement model according to an example of the present disclosure.

The built environment dominant color measurement model is constructed and trained by taking sensitivity data and a dominant color feature as an input, which specifically includes:

the built environment image and electroencephalogram sensitivity data thereof are converted into several build environment sequence samples, the built environment dominant color measurement model (as shown in FIG. 5) is constructed through an XGBoost decision tree algorithm, 75% percent of built environment sample data are trained, and remaining sample data are taken as a test set;

environment dominant color features of eight dimensions are fused through a concat method to obtain an overall environment dominant color feature $H_{all}$;

the sensitivity data and the dominant color feature parameter are input into the built environment dominant color measurement model, which is specifically as follows:

$Z=\{(H_i, y_i)|i=1,2,\ldots,n\}$ where $H_i$ denotes an overall environment dominant color feature of an $i^{th}$ image sample, $y_i$ denotes a dominant color sensitivity value of the image sample, and n denotes the number of the image sample; and a Kaiser-Meyer-Olkin (KMO) test and a Bartlett's test of sphericity are performed on an input feature parameter, and if a KMO value of a data result is greater than 0.5 and a probability P value of the Bartlett's test of sphericity is less than 0.05, a parameter of the dominant color measurement model may be set.

In the present example, when the built environment dominant color measurement model is trained, a parameter of the decision tree algorithm is optimized through a random search algorithm. A network parameter setting value is as shown in Table 2. Then a hyperparameter is optimized according to a model evaluation index, and the model is further evaluated (see Table 3) through K-fold cross-validation, a determination coefficient ($R^2$), a mean absolute error (MAE), and a root mean square error (RMSE). The greater the $R^2$ is, the better the effect of the model is, and the smaller the MAE and the RMSE are, the more accurate the model prediction is.

In order to control an iteration rate and prevent overfitting, a parameter learning_rate is employed to control the iteration rate, and a LightGBM algorithm is employed to accelerate a training process on the premise of ensuring the precision.

TABLE 2

| XGBoost decision tree algorithm parameter setting | | | |
| --- | --- | --- | --- |
| Parameter name | Meaning | Parameter optimization range | Random search setting |
| n_estimators | number of basic evaluators (number of iterations) | 1-800 | 600 |
| learning_rate | learning_rate (control iteration rate) | 0.01-0.5 | 0.5 |
| max_depth | maximum depth of tree | 1-10 | 5 |
| Gamma | minimum loss function descent value | 0-1 | 0.4 |
| Subsample | proportion for training data | 0-1 | 1 |
| min_child_weight | minimum sample size on leaf | 0-10 | 3 |
| random_state | Number of seed | 0-10 | 10 |
| reg_alpha | weight of L1 regularization term | 0, 1 | 0 |
| reg_lambda | weight of L2 regularization term | 0, 1 | 1 |

TABLE 3

Performance evaluation result of built environment dominant color measurement model under K-fold cross-validation

| | Number of 10-fold cross-validation | | |
| --- | --- | --- | --- |
| | MAE | RESM | $R^2$ |
| 1 | 25.698 | 86.054 | 0.947 |
| 2 | 25.243 | 70.214 | 0.958 |
| 3 | 24.337 | 66.452 | 0.943 |
| 4 | 25.896 | 78.698 | 0.923 |
| 5 | 28.214 | 93.334 | 0.945 |
| 6 | 28.345 | 128.423 | 0.954 |
| 7 | 25.642 | 73.162 | 0.943 |
| 8 | 25.476 | 78.562 | 0.937 |
| 9 | 28.942 | 127.523 | 0.954 |
| 10 | 28.642 | 96.811 | 0.961 |
| Average | 26.6435 | 89.9233 | 0.948 |

An environment image to be analyzed is input into a trained model, so as to obtain a predicted dominant color sensitivity result, which specifically includes:

a nonlinear regression model for predicting the built environment dominant color is acquired as follows by taking the hue proportion (HS), the saturation proportion (BS), the lightness proportion (VS), the maximum color cluster area (MCA), the color cluster shape complexity (CDS), the color cluster diversity (NPC), the color cluster segmentation degree (DPS), and the similar color cluster spread degree (IPS) as influence indexes:

$$\widetilde{Prec}_{XGBoost} = f_{XGBoost}(HS,BS,VS,MCA,NPC,CDS,DPC,IPS)$$

where $\widetilde{Prec}_{XGBoost}$ denotes predicted dominant color sensitivity data, $\widetilde{Prec}_{XGBoost}$ $\epsilon(0,100]$;

a loss function is applied as follows, so as to make a finally-trained weight smoother, thereby avoiding an overfitting phenomenon:

$$L(\varphi) = \sum_i l(y_i, \hat{y}_i) + \sum_m \left(\eta T + \frac{1}{2}\rho\|\omega\|^2\right) + c$$

where $L(\varphi)$ denotes a set of differences between all predicted parameters and an actual parameter of a model regression tree, $l(y_i,\hat{y}_i)$ denotes a difference between a predicted measurement parameter and a target parameter, $$\eta T + \frac{1}{2}\rho\|\omega\|^2$$

denotes a regularization term optimization function for avoiding overfitting, T denotes the number of a leaf node of the regression tree, $\omega$ denotes a score of each leaf node, and $\eta$ and $\rho$ denote coefficients with parameters to be adjusted;

in the present example, when the environment dominant color feature is fused, a predicted evaluation result of any feature and dominant color sensitivity evaluation results of a plurality of sample images may be input into a preset loss function to obtain an error between a predicted result and an evaluation result of an environment dominant color fusion feature. The error is an output of the preset loss function, thereby determining whether the training model converges;

a dominant color feature importance score of the model is calculated, which is specifically as follows:

$$F(i) = \frac{\left(\bar{x}_i^{(+)} - \bar{x}_i\right)^2 + \left(\bar{x}_i^{(-)} - \bar{x}_i\right)^2}{\frac{1}{n_+ - 1}\sum_{r=1}^{n_+}\left(x_{r,i}^{(+)} - \bar{x}_i^{(+)}\right)^2 + \frac{1}{n_- - 1}\sum_{r=1}^{n_-}\left(x_{r,i}^{(-)} - \bar{x}_i^{(-)}\right)^2}$$

where $\bar{x}_i$ denotes an average of an ith dominant color feature value of the sample, $$\bar{x}_i^{(+)} \text{ and } \bar{x}_i^{(-)}$$

denote averages of feature values of all positive samples and all negative samples, respectively, and r denotes an instance corresponding to an ith environment dominant color feature; and the greater the F(i) is, the greater the feature influence on the dominant color sensitivity is, so that a crucial landscape color feature may be screened, and an environment dominant color quantification system may be constructed comprehensively, thereby improving an environment planning and design quality; and a dominant color feature weight of the model is calculated, and an environment dominant color quality is evaluated according to the feature weight, a specific processing process of which is as follows:

$$w_t^* = \frac{-\sum_{i=1}^{n} G_i}{\sum_{i=1}^{n} H_i + \lambda}$$

where $$w_t^*$$

denotes a weight value of a tth environment dominant color feature of the sample, $$\sum_{i=1}^{n} G_i$$

denotes the sum of gradient statistics of all leaf samples of the model regression tree, and $$\sum_{i=1}^{n} H_i + \lambda$$

denotes the sum of second order statistics of all the leaf samples of the model regression tree; where
a calculation process of an environment dominant color quality score is as follows:

$$H_{quality} =$$

$$n \cdot w_1 H_1 + 5 \cdot w_2 H_2 + 4 \cdot w_3 H_3 + w_4 H_4 + w_5 H_5 + + w_6 H_6 + w_7 H_7 + w_8 H_8$$

where n denotes the total number of a hue of the color cluster, w denotes the weight value of the dominant color feature, H denotes the dominant color feature parameter, and a final environment dominant color quality score is acquired by normalizing $H_{quality}$.

Figure 6:
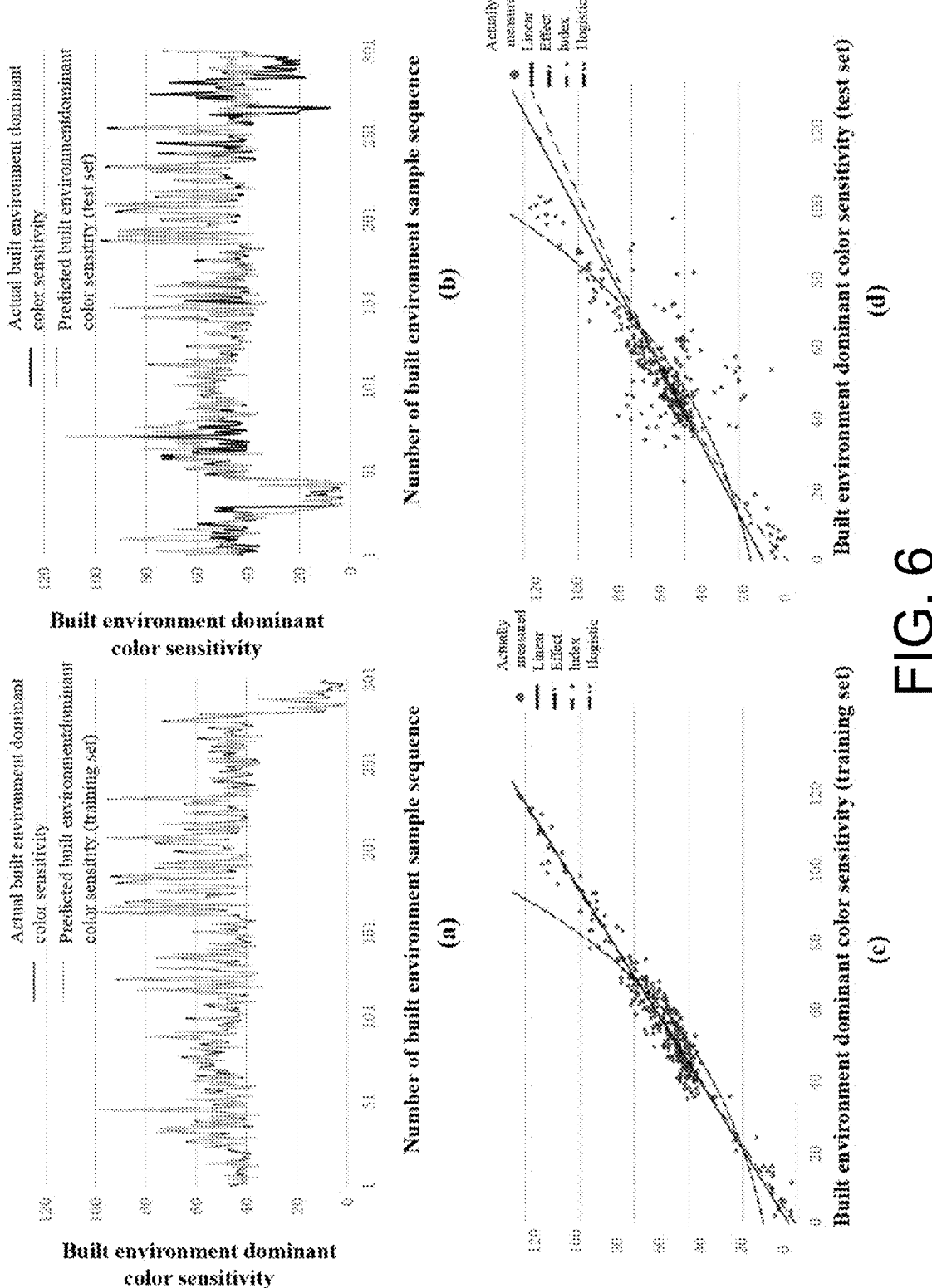
FIG. 6 is a fitting curve diagram of a predicted environment sensitivity and an actual environment sensitivity of a measurement model according to an example of the present disclosure.

In the present example, the color feature importance score is calculated through the model. Scores of the maximum color cluster area, the color cluster segmentation degree, the hue proportion, the color cluster diversity, the similar color cluster spread degree, the saturation proportion, the lightness proportion, and the color cluster shape complexity are 8486.848, 4135.527, 3665.604, 1270.764, 764.674, 474.965, 440.531, and 205.862, respectively (Table 4). Therefore, it may be seen from the analysis results in FIGS. 5 and 6 that a maximum color cluster area, a color cluster segmentation degree, a hue proportion, and color cluster diversity of a landscape color should be focused in landscape color planning and design. Some predicted results of the built environment samples are shown in FIG. 6. 9.28% of the built environment image samples have the dominant color sensitivity (ATD)≥70, and 78% of the image samples have the dominant color sensitivity (ATD)≥40, which may be deemed as landscapes drawing certain attention. In this case, on the basis of the dominant color sensitivity value (the greater the dominant color sensitivity is, the more likely the color matching effect is to excite people's attention and interest). Therefore, the landscape with a lower sensitivity is selected for update and design.

TABLE 4

| Environment dominant color feature weight and importance distribution | | |
|---|---|---|
| Feature name | Weight value | Importance value |
| Hue proportion (HS) | 0.18 | 3665.604 |
| Saturation proportion (BS) | 0.07 | 474.965 |
| Lightness proportion (VS) | 0.04 | 440.531 |
| Maximum color cluster area (MCA) | 0.13 | 8486.848 |
| Color cluster diversity (NPC) | 0.10 | 1270.764 |
| Color cluster shape complexity (CDS) | 0.06 | 205.862 |
| Color cluster segmentation degree (DPS) | 0.27 | 4135.527 |
| Similar color cluster spread degree (IPS) | 0.15 | 764.674 |

Example 2

The present example provides measurement system based on image electroencephalogram sensitivity data for a built environment dominant color. The system includes:
  a data collection processing module configured to acquire several built environment images and electroencephalogram data corresponding thereto, and convert same into several build environment image sequence samples;
  an electroencephalogram sensitivity extraction module configured to extract an electroencephalogram sensitivity index from the electroencephalogram data, so as to obtain a built environment dominant color sensitivity value;
  a dominant color feature extraction module configured to identify and segment an image color from an image sample, so as to obtain an image color cluster and a dominant color feature parameter;
  an environment dominant color measurement model training module configured to construct a built environment dominant color measurement model, input sensitivity data and the dominant color feature parameter, and train the model through an XGBoost decision tree algorithm;
  a feature importance identification module configured to identify an important dominant color feature, and construct a comprehensive environment dominant color measurement system according to an environment dominant color feature selection table; and
  a quality quantitative evaluation module applied to a built environment measurement method and configured to evaluate an environment dominant color quality according to a dominant color feature weight.

The electroencephalogram sensitivity extraction module specifically includes:
  an electroencephalogram signal pre-processing unit configured to perform filtering and artifact correction on original electroencephalogram data, remove data with amplitudes beyond an interval range of 10 μV-100 μV as a bad lead, and perform re-classification and superposed averaging according to the image sample;
  an electroencephalogram frequency band extraction unit configured to extract average relative power spectra of frequency bands α, β, and θ of eight leads;
  a sensitivity index calculation unit configured to calculate an electroencephalogram sensitivity index from an electroencephalogram feature; and a dominant color sensitivity acquisition unit configured to acquire a built environment dominant color sensitivity value as training data of the environment dominant color measurement model.

The dominant color feature extraction module includes:

a sample image processing unit configured to perform data dimension conversion on the image sequence sample;

a color cluster extraction unit configured to identify and segment a color of the image sequence sample, so as to obtain saturation, lightness, brightness, and a channel of the image sample, and an area and a perimeter of a color cluster block;

a dominant color feature selection unit configured to construct an environment dominant color feature including a hue proportion, a saturation proportion, a lightness proportion, a maximum color cluster area, color cluster, shape complexity, color cluster diversity, a color cluster segmentation degree, and a similar color cluster spread degree;

a feature parameter calculation unit configured to calculate each dominant color feature parameter; and a normalization unit configured to encode the dominant color feature as an input feature of the built environment dominant color measurement model, so that the environment dominant color feature parameter falls within an interval [0, 1].

The environment dominant color measurement model training module specifically includes:

an environment dominant color measurement model construction unit configured to construct an environment dominant color sensitivity and dominant color feature measurement model through an XGBoost decision tree algorithm;

a feature fusion unit configured to accelerate a training process;

an environment dominant color measurement model training unit configured to train a nonlinear regression model taking an environment dominant color feature as an influence index, where during training, an iteration rate is controlled through a parameter learning_rate, thereby preventing overfitting, and a training process is accelerated through a LightGBM algorithm on the premise of ensuring the precision; and an environment dominant color sensitivity prediction unit configured to input built environment image data to be predicted into a trained environment dominant color measurement model, so as to obtain a predicted built environment dominant color sensitivity.

Beneficial Effect

According to the measurement method and system based on image electroencephalogram sensitivity data for a built environment dominant color of the present disclosure, the problems that the prediction effect of the nonlinear model integrating the image color feature and the environment quality remains to be improved; and moreover, the conventional environment image evaluation features the complicated process and the extreme long overall flow cycle, and accordingly, the dominant color information can hardly be fed back synchronously, affecting the accuracy and efficiency of the environment dominant color quality prediction are effectively solved.

It is to be noted that relation terms such as first and second are merely used to distinguish one entity or operation from another entity or operation herein, and do not necessarily require or imply any such an actual relation or order between these entities or operations. Moreover, terms "comprise", "include", "encompass", or their any other variants are intended to cover non-exclusive inclusion. Therefore, a process, method, article, or apparatus including a series of elements include those elements, as well as other elements not listed clearly, or further include elements inherent to such a process, method, article, or apparatus. Without more limitations, the element limited by the sentence "include a . . . " does not exclude that the process, method, article, or apparatus including the element further includes another same element.

What is claimed is:

1. A measurement method based on image electroencephalogram sensitivity data for a built environment dominant color, comprising:

acquiring electroencephalogram data corresponding to a built environment image sample, comprising:

collecting electroencephalogram data of J subjects on I built environment images under the same laboratory environment to obtain I*J electroencephalogram data groups, wherein a data size of each data group is $n^{(d)}$, d denotes a dominant color feature dimension of each data group, and n denotes the number of an electroencephalogram data sample collected at a time;

calculating an environment dominant color sensitivity on the basis of the electroencephalogram data, specifically comprising:

selecting electroencephalogram signals, generated within 3 seconds before and after stimulation of the built environment image sample, of eight leads of occipital lobe regions O1, OZ, O2, POZ, PO3, PO4, PO7, and PO8;

acquiring difference wave data before and after sample visual stimulation through original electroencephalogram data;

performing short-time Fourier transform on an electroencephalogram signal of each lead, and extracting power spectral densities of frequency band $\alpha$ of 8 Hz-13 Hz, frequency band $\beta$ of 14 Hz-41 Hz, and frequency band $\theta$ of 4 Hz-8 Hz of pre-processed electroencephalogram data, respectively;

calculating an electroencephalogram sensitivity index according to average relative power spectra of frequency bands $\alpha$, $\beta$, and $\theta$, so as to obtain a built environment dominant color sensitivity of the image sample, a calculation process of which is as follows:

$$E_{FT} = \frac{1}{8} \sum_k \frac{P_\theta(k) + P_\alpha(k)}{P_\beta(k)}$$

wherein $E_{FT}$ denotes the electroencephalogram sensitivity index, $1 \leq k \leq 8$ denoting the eight leads, and $P_\theta(k)$, $P_\alpha(k)$, and $P_\beta(k)$ denote the average relative power spectra of frequency bands $\alpha$, $\beta$, and $\theta$ of the lead, respectively; and nondimensionalizing an electroencephalogram sensitivity index according to an influence from an individual difference of the subject, which is specifically as follows:

$$Z_j(i) = z_j(i) / \frac{1}{n} \sum_{j=1}^{n} z_j(i)$$

wherein $Z_j(i)$ denotes a nondimensionalized electroencephalogram sensitivity of a $j^{th}$ subject on an ith image sample, and n denotes the number of the image sample; wherein a built environment dominant color sensitivity value is as follows:

$$E_{AT} = \frac{1}{Z_j(i)} * 100\%$$

wherein $E_{AT}$ denotes the built environment dominant color sensitivity of the image sample;

extracting a dominant color feature parameter according to the built environment image sample;

constructing a built environment dominant color measurement model, and training the built environment dominant color measurement model by taking sensitivity data and a dominant color feature as an input;

extracting a dominant color feature parameter from an environment image to be analyzed; and inputting the dominant color feature parameter into the trained built environment dominant color measurement model, so as to obtain a predicted dominant color sensitivity result.

2. The measurement method based on image electroencephalogram sensitivity data for a built environment dominant color according to claim 1, wherein the extracting a dominant color feature parameter according to the built environment image sample specifically comprises:

performing data dimension conversion on an image sample $\{i_1, i_2, \ldots, i_m\}$ to set a size of a zoomed image to 1024 pixels×600 pixels;

identifying and segmenting a color of the image, and outputting color cluster division D=$\{d_1, d_2, \ldots, d_k\}$, which is specifically as follows:

$$S = \sum_{n=1}^{N}\sum_{k=1}^{K} r_{nk}\|Q(n) - d_k\|^2$$

$$d_k = \frac{1}{T_k}\sum_{i=1}^{T_k} Q(n)$$

wherein S denotes the sum of distortion degrees of all color clusters, Q(n) denotes a color value of the pixel, N denotes the number of a pixel of the color cluster, n denotes coordinates of a pixel point of an environment image, $d_k$ denotes a centroid of a color of type k, K denotes the number of the color cluster, $r_{nk}$ denotes two components configured to determine whether Q(n) belongs to the color of type k, and $T_k$ denotes the number of a pixel of a $k^{th}$ color cluster;

acquiring all color names associated with an image color cluster according to an image sample color extraction result, and calculating saturation, lightness, brightness, a channel of a $\{k_1, k_2, \ldots, k_j\}$th color type of the image sample, and an area and a perimeter of a color cluster block, wherein a boundary of the color cluster block is calculated on the basis of an average of a pixel color and smoothed moderately to avoid a measurement error caused by simplifying the boundary;

constructing the environment dominant color feature parameter comprising a hue proportion, a saturation proportion, a lightness proportion, a maximum color cluster area, color cluster shape complexity, color cluster diversity, a color cluster segmentation degree, and a similar color cluster spread degree; and performing min-max normalization processing on an environment dominant color feature, which is specifically as follows:

$$H_{std} = \frac{H_{int} - \min\ (H_{int})}{\max\ (H_{int}) - \min\ (H_{int})}$$

wherein $H_{std}$ denotes a feature value before normalization, and $H_{int}$ denotes a result of a normalized feature value.

3. The measurement method based on image electroencephalogram sensitivity data for a built environment dominant color according to claim 2, wherein the constructing a built environment dominant color measurement model, and training same by taking sensitivity data and a dominant color feature as an input specifically comprises:

converting the built environment image and electroencephalogram sensitivity data thereof into several build environment sequence samples, constructing the built environment dominant color measurement model through an XGBoost decision tree algorithm, training 75% of sequence sample data, and taking remaining sequence sample data as a test set;

fusing environment dominant color features of eight dimensions through a concat method to obtain an overall environment dominant color feature $H_{all}$;

inputting the sensitivity data and the dominant color feature parameter into the built environment dominant color measurement model, which is specifically as follows:

$$Z=\{(H_i, y_i)|i=1,2, \ldots, n\}$$

wherein $H_i$ denotes an overall environment dominant color feature of an $i^{th}$ image sample, $y_i$ denotes a dominant color sensitivity value of the image sample, and n denotes the number of the image sample; and performing a Kaiser-Meyer-Olkin test and a Bartlett's test of sphericity on an input feature parameter.

4. The measurement method based on image electroencephalogram sensitivity data for a built environment dominant color according to claim 3, wherein the inputting an environment image to be analyzed into a trained model, so as to obtain a dominant color sensitivity predicted result specifically comprises:

acquiring a nonlinear regression model for predicting the built environment dominant color as follows by taking the hue proportion, the saturation proportion, the lightness proportion, the maximum color cluster area, the color cluster shape complexity, the color cluster diversity, the color cluster segmentation degree, and the similar color cluster spread degree as influence indexes:

$$\widehat{Prec}_{XGBoost} = f_{XGBoost}(HS, BS, VS, MCA, NPC, CDS, DPC, IPS)$$

wherein $\widehat{Prec}_{XGBoost}$ denotes predicted dominant color sensitivity data, $\widehat{Prec}_{XGBoost} \in (0,100]$, HS denotes the hue proportion, BS denotes the saturation proportion, VS denotes the lightness proportion, MCA denotes the maximum color cluster area, DPS denotes the color cluster segmentation degree, NPC denotes the color cluster diversity, IPS denotes the similar color cluster spread degree, and CDS denotes color cluster shape complexity;

applying a loss function as follows, so as to make a finally-trained weight smoother, thereby avoiding an overfitting phenomenon:

$$L(\varphi) = \sum_i l(y_i, \hat{y}_i) + \sum_m \left( \eta T + \frac{1}{2} \rho \|\omega\|^2 \right) + c$$

wherein $L(\varphi)$ denotes a set of differences between all predicted parameters and an actual parameter of a model regression tree, $l(y_i, \hat{y}_i)$ denotes a difference between a predicted measurement parameter and a target parameter, $$\eta T + \frac{1}{2} \rho \|\omega\|^2$$

denotes a regularization term optimization function for avoiding overfitting, T denotes the number of a leaf node of the regression tree, $\omega$ denotes a score of each leaf node, and $\eta$ and $\rho$ denote coefficients with parameters to be adjusted;

calculating a dominant color feature importance score F(i) of the model, which is specifically as follows:

$$F(i) = \frac{\left( \overline{x}_i^{(+)} - \overline{x}_i \right)^2 + \left( \overline{x}_i^{(-)} - \overline{x}_i \right)^2}{\frac{1}{n_+ - 1} \sum_{r=1}^{n_+} \left( x_{r,i}^{(+)} - \overline{x}_i^{(+)} \right)^2 + \frac{1}{n_- - 1} \sum_{r=1}^{n_-} \left( x_{r,i}^{(-)} - \overline{x}_i^{(-)} \right)^2}$$

wherein $\overline{x}_i$ denotes an average of an ith dominant color feature value of the built environment sequence sample, $$\overline{x}_i^{(+)} \text{ and } \overline{x}_i^{(-)}$$

denote averages of feature values of all positive samples and all negative samples, respectively, and r denotes an instance corresponding to an $i^{th}$ environment dominant color feature; and calculating a dominant color feature weight of the model, and evaluating an environment dominant color quality according to the feature weight, a specific processing process of which is as follows:

$$w_t^* = \frac{-\sum_{i=1}^n G_i}{\sum_{i=1}^n H_i + \lambda}$$

wherein $$w_t^*$$

denotes a weight value of a $t^{th}$ environment dominant color feature of the built environment sequence sample, $$\sum_{i=1}^n G_i$$

denotes the sum of gradient statistics of all leaf samples of the model regression tree, and $$\sum_{i=1}^n H_i + \lambda$$

denotes the sum of second order statistics of all the leaf samples of the model regression tree; wherein a calculation formula of an environment dominant color quality score is as follows:

$$H_{quality} =$$
$$n \cdot w_1 H_1 + 5 \cdot w_2 H_2 + 4 \cdot w_3 H_3 + w_4 H_4 + w_5 H_5 + + w_6 H_6 + w_7 H_7 + w_8 H_8$$

wherein n denotes the total number of a hue of the color cluster, w denotes the weight value of the dominant color feature, H denotes the dominant color feature parameter, and a final environment dominant color quality score is acquired by normalizing $H_{quality}$.

5. A measurement system based on image electroencephalogram sensitivity data for a built environment dominant color, comprising:

a processor, configured to execute:

a data collection processing module to acquire several built environment images and electroencephalogram data corresponding thereto, and convert same into several build environment sequence samples;

an electroencephalogram sensitivity extraction module to extract an electroencephalogram sensitivity index from the electroencephalogram data, so as to obtain a built environment dominant color sensitivity value, wherein the electroencephalogram sensitivity extraction module specifically comprises:

an electroencephalogram signal pre-processing unit, executed by the processor to perform filtering and artifact correction on original electroencephalogram data, remove data with amplitudes beyond an interval range of 10 μV-100 μV as a bad lead, and perform re-classification and superposed averaging according to the image sample;

an electroencephalogram frequency band extraction unit, executed by the processor to extract average relative power spectra of frequency bands α, β, and θ of eight leads;

a sensitivity index calculation unit, executed by the processor to calculate an electroencephalogram sensitivity index from an electroencephalogram feature; and a dominant color sensitivity acquisition unit, executed by the processor to acquire a built environment dominant color sensitivity value as training data of the environment dominant color measurement model;

a dominant color feature extraction module to identify and segment an image color from an image sample, so as to obtain an image color cluster and a dominant color feature parameter;

an environment dominant color measurement model training module to construct a built environment dominant color measurement model, input sensitivity data and the dominant color feature parameter, and train the model through an XGBoost decision tree algorithm;

a feature importance identification module to identify an important dominant color feature, and construct a comprehensive environment dominant color measurement system according to an environment dominant color feature selection table; and a quality quantitative evaluation module applied to a built environment measurement method, wherein the quality quantitative evaluation module is executed by the processor to evaluate an environment dominant color quality according to a dominant color feature weight.

6. The measurement system based on image electroencephalogram sensitivity data for a built environment dominant color according to claim 5, wherein the dominant color feature extraction module comprises:

a sample image processing unit configured to perform data dimension conversion on the image sample;

a color cluster extraction unit configured to identify and segment a color of the image sample, so as to obtain saturation, lightness, brightness, and a channel of the image sample, and an area and a perimeter of a color cluster block;

a dominant color feature selection unit configured to construct an environment dominant color feature comprising a hue proportion, a saturation proportion, a lightness proportion, a maximum color cluster area, color cluster shape complexity, color cluster diversity, a color cluster segmentation degree, and a similar color cluster spread degree;

a feature parameter calculation unit configured to calculate each dominant color feature parameter; and a normalization unit configured to encode the dominant color feature as an input feature of the built environment dominant color measurement model, so that the environment dominant color feature parameter falls within an interval [0,1].

7. The measurement system based on image electroencephalogram sensitivity data for a built environment dominant color according to claim 5, wherein the environment dominant color measurement model training module specifically comprises:

an environment dominant color measurement model construction unit configured to construct an environment dominant color sensitivity and dominant color feature measurement model through an XGBoost decision tree algorithm;

a feature fusion unit configured to accelerate a training process;

an environment dominant color measurement model training unit configured to train a nonlinear regression model taking an environment dominant color feature as an influence index; and an environment dominant color sensitivity prediction unit configured to input built environment image data to be predicted into a trained environment dominant color measurement model, so as to obtain a predicted built environment dominant color sensitivity.

* * * * *